(12) United States Patent
Bartholomew et al.

(10) Patent No.: US 6,700,484 B2
(45) Date of Patent: Mar. 2, 2004

(54) NETWORKED MINIATURE CHEMICAL OPTICAL SENSORS

(75) Inventors: Dwight Urban Bartholomew, Dallas, TX (US); Diane L. Arbuthnot, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 412 days.

(21) Appl. No.: 09/732,335

(22) Filed: Dec. 7, 2000

(65) Prior Publication Data

US 2002/0070854 A1 Jun. 13, 2002

Related U.S. Application Data

(60) Provisional application No. 60/173,643, filed on Dec. 30, 1999.

(51) Int. Cl.[7] .................................................. G08B 1/00
(52) U.S. Cl. .................. 340/531; 340/600; 340/632; 340/633; 342/326; 342/329; 73/579; 73/587
(58) Field of Search ................................ 340/531, 600, 340/632, 633; 250/369; 324/329, 326; 73/579, 587

(56) References Cited

U.S. PATENT DOCUMENTS

| | | | | |
|---|---|---|---|---|
| 4,931,646 A | * | 6/1990 | Koechner | 250/367 |
| 5,828,059 A | * | 10/1998 | Udd | 250/227.18 |
| 5,898,373 A | * | 4/1999 | Murad et al. | 340/600 |

OTHER PUBLICATIONS

"Detection of a polynitroaromatic compound using a novel polymer–based multiplate sensor," SPIE Conference on Detection and Remediation Technologies for Mines and Minelike Targets III, Orlando, Florida, Apr. 1998, pp. 432–440 (Diane Arbuthnot; Dwight Bartholomew; Richard Carr; Jerome L. Elkind; Liliana Gheorghiu; Jose L. Melendez; and W. Rudolf Seitz,.

\* cited by examiner

*Primary Examiner*—Daryl Pope
(74) *Attorney, Agent, or Firm*—David Denker; Wade James Brady, III; Frederick J. Telecky, Jr.

(57) ABSTRACT

A network for detecting a substance includes at least two detectors that are capable of transmitting a signal, and a remote station capable of receiving the signal. The detectors are adapted to detect a substance and transmit data that indicates the presence of that substance to the remote receiving station.

20 Claims, 3 Drawing Sheets

NETWORKED MINIATURE CHEMICAL OPTICAL SENSORS

CROSS-REFERENCE TO RELATED APPLICATIONS

This application claims priority from Provisional Application No. 60/173,643, filed Dec. 30, 1999.

The following applications contain subject matter related to the present application and are assigned to the assignee of the present application: co-file applications with Ser. Nos. 09/732,248 and 09/732,338.

GOVERNMENT CONTRACT

This invention was made with Government support under Defense Applied Research Projects Agency contract number DABT63-97-C-0018. The Government has certain rights in this invention.

TECHNICAL FIELD OF THE INVENTION

The present invention relates in general to sensors, and in particular, to a network of miniature chemical optical sensors for measuring and detecting gases.

BACKGROUND OF THE INVENTION

Without limiting the scope of the invention, its background is described in connection with land mine detection, as an example.

Anti-personnel mines, commonly called land mines, cause severe injuries and casualties to thousands of civilians and military troops around the world each year. There are over 120 million land mines currently deployed in over 60 countries around the world. Each year, over 2 million new land mines 20 are laid, while only about 100,000 mines are cleared.

These mines are typically deployed randomly within a strategic area and may be buried or camouflaged so they are invisible to a casual observer. Mines may instantly and indiscriminately claim unsuspecting victims who step or drive on the mine's triggering mechanism. The clandestine and indiscriminate nature of land mines make them a particularly dangerous weapon for anyone in close proximity to the mine.

Mines contain an explosive, which rapidly accelerates shrapnel or other projectiles when activated. Many mines contain trinitrotolulene (TNT), which is a common explosive compound. TNT and other explosives are polynitroaromatic compounds that emit a vapor. This emitted vapor may be useful to detect mines and other explosives.

Current detection methods range from high-tech electronic (ground penetrating radar, infra-red, magnetic resonance imaging) to biological detection schemes (dog sniffers and insects or bacteria) to simple brute force detonation methods (flails, rollers and plows) and the use of hand-held mechanical prodders. Most of these methods are very slow and/or expensive and suffer from a high false alarm rate. Mines usually do not possess self-destroying mechanisms and due to their long active time jeopardize the lives of millions of people. Furthermore, mines are difficult to find with commercial metal detectors, because their metal content is very low and in some cases even zero.

SUMMARY OF THE INVENTION

Therefore, a system that detects mines having little or no metallic content is now needed; providing enhanced design performance and accuracy while overcoming the aforementioned limitations of conventional methods.

Generally, and in one form of the invention, a network for detecting a substance including at least two detectors that are capable of transmitting a signal, and a remote station capable of receiving the signal is disclosed. The detectors are adapted to detect a substance and transmit data that indicates the presence of that substance to the remote receiving station.

In one embodiment of the present invention, the detectors are adapted to detect a vapor.

In another embodiment of the present invention, the detectors are capable of receiving the transmitted signal.

In yet another embodiment of the present invention, the detectors have a light detector and a waveguide.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

For purposes of illustration, a vapor detector that uses a polymer waveguide sensitive to polynitroaromatic compounds is provided. The principles and applications of the present invention are not limited only to detecting explosives; being applicable to detection of radiation, a variety of vapors from many different substances or both, or contaminants in liquids or solutions.

Figure 1:
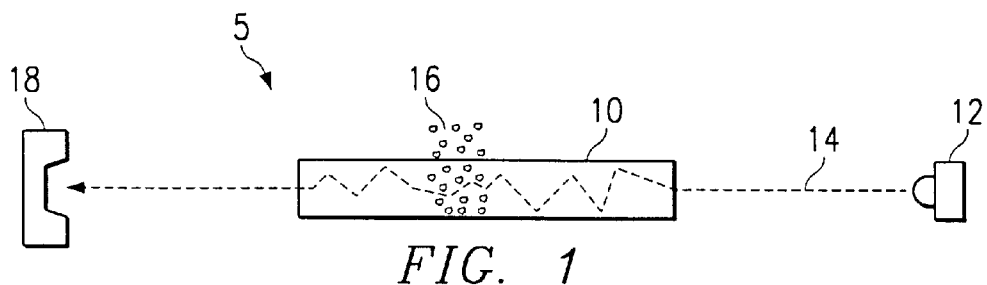
FIG. 1 is a schematic of a vapor detector.

Referring now to FIG. 1, a schematic representative of a vapor detector 5 is shown. A waveguide 10 may be formed from a variety of polymer compounds, such as polyvinylchloride (PVC), for example, that are suitable for producing an optically clear structure. The waveguide 10 is impregnated or infused with a chemical, Jeffamine T-403 (developed by TEXACO) for example, that reacts with vapor from the compound to be detected.

In this specific example, Jeffamine also acts as a plasticizer for the PVC compound. Inherent rigidity in the PVC compound allows the waveguide 10 to be self-supporting. A self-supporting waveguide 10 simplifies production and reduces associated costs of the device. The waveguide 10, alternatively, may be deposited on a substrate (shown in FIG. 2).

For example, in operation, the vapor detector 5 may be used as follows. Many land mines contain TNT, which is a polynitroaromatic compound. Jeffamine T-403 reacts with TNT vapor thereby altering the light absorbent properties of the waveguide 10. Other chemicals may be mixed with the polymer of the waveguide 10 to allow the vapor detector 5 to detect other compounds. The vapor detector 5 may also incorporate several waveguides 10 to detect multiple compounds at a single location.

A light source 12 may be used to emit light 14 into waveguide 10. The light source 12 may be an incandescent lamp, an LED, a laser or any other light producing device known in the art. Vapor 16 that has reacted with chemicals within waveguide 10 absorbs some of the light 14. The remainder of light 14 passes through waveguide 10 into a light detector 18.

Light detector 18 analyzes the characteristics of the light 14 that is transmitted through the waveguide 10, which has been exposed to vapor 16, to identify the compound that emitted vapor 16. Light detector 18 may be a semiconductor photo-detector, a photo-multiplier tube, a bolometer or other heat or light-sensitive detector known in the art.

Figure 2:
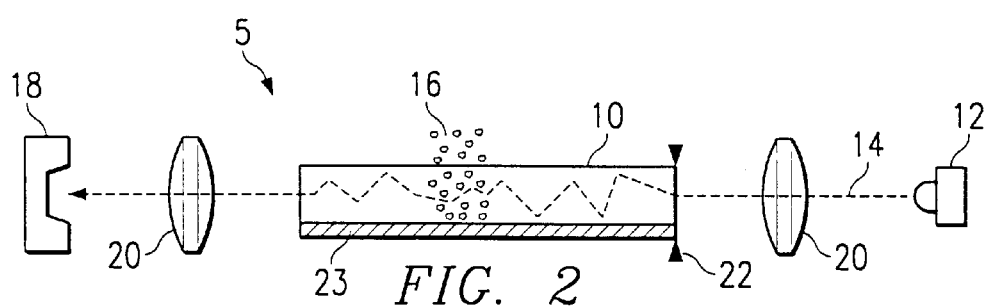
FIG. 2 is a schematic of a vapor detector having a focused light source.

Now referring to FIG. 2, an alternative embodiment of the invention is illustrated. Light 14 from light source 12 may be focused with one or more lenses 20 to obtain a more accurate transmission of light 14 through waveguide 10. A light block 22 may be used to direct light 14 into waveguide 10 and eliminate any stray light from sources other than the intended light source 12. A reflective region 23 may be included on the waveguide 10 to further enhance the intensity of transmitted light 14. The reflective region 23 may be made from Polished metal or any other suitable reflective material.

Figure 3:
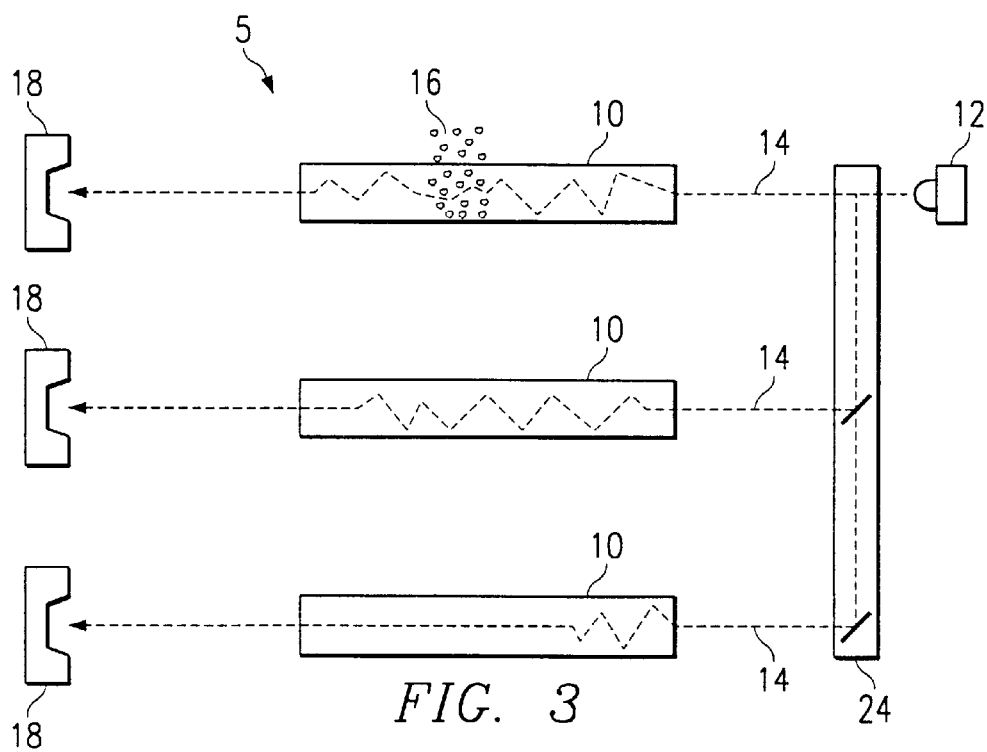
FIG. 3 is a schematic of a multiple vapor detector.

Another embodiment of the invention is illustrated in FIG. 3. A beam splitter 24 may be used to create multiple beams of light 14 from a single light source 12. These multiple beams of light 14 may be directed into multiple different waveguides 10 by lenses 20 and light blocks 22. The light 14 is transmitted through the waveguides 10 into multiple light detectors 18. Each waveguide 10 may be compounded with a different chemical to detect a unique compound. A vapor detector 5 with multiple, individually configured waveguides 10 could detect the presence of several different compounds located in a single area.

Figure 3A:
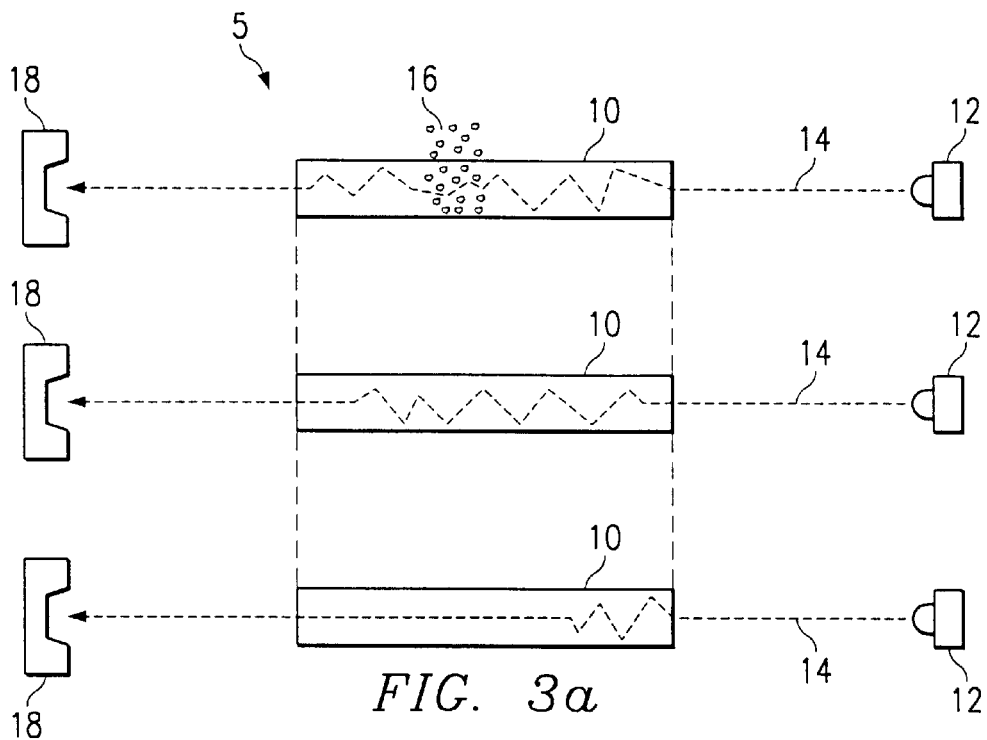
FIG. 3a is a schematic of a multiple vapor detector.

Another embodiment of the invention is illustrated in FIG. 3a. Multiple beams of light 14 may be directed into multiple different waveguides 10 by multiple light sources 12. Multiple beams of light 14 are transmitted through the waveguides 10 into multiple light detectors 18. Each waveguide 10 may be compounded with a different chemical to detect a unique compound. Each light source 12 may emit a different wavelength of light, which is also designed to detect a unique compound. Alternatively, as indicated by the dotted lines, one embodiment of the invention may have a single waveguide 10.

Figure 4:
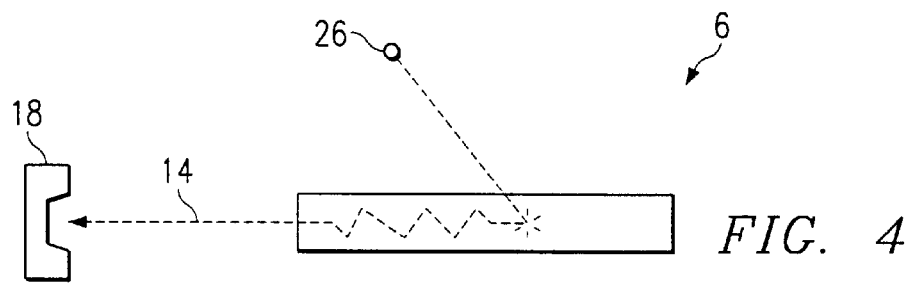
FIG. 4 is a schematic of a radiation detector.

Now referring to FIG. 4, a radiation detector 6 may contain waveguide 10, which may contain a chemical that emits light when exposed to radiation. Radioactive particle 26 impinges waveguide 10 and causes a reaction with a chemical in the waveguide 10 that produces light 14. The light 14 is transmitted through waveguide 10 and into light detector 18. Light detector 18 analyzes the characteristics of the light 14 that is transmitted through the waveguide 10, and signals the presence of radiation within the area.

The source radiation must be converted into visible light prior to its detection by light detector 18. This is accomplished by a scintillation chemical compounded in the waveguide 10. A scintillation chemical is a material that emits optical photons in response to ionizing radiation. Optical photons are photons with energies corresponding to wavelengths between 3,000 and 8,000 angstroms. Thus, the scintillation compound converts source radiation energy from radioactive particle 26 into visible light energy, which may then be detected by the light detector 18.

Examples of scintillation layer material for this application may include: $GdO_2$ $S_2$, CsI, CsI:TI, $BaSO_4$, $MgSO_4$, $SrSO_4$, $Na_2$ $SO_4$, $CaSO_4$, BeO, LiF, $CaF_2$, etc. A more inclusive list of such materials is presented in U.S. Pat. No. 5,418,377, which is incorporated herein by reference. Commercial scintillation layers may contain one or more of these materials.

Figure 5:
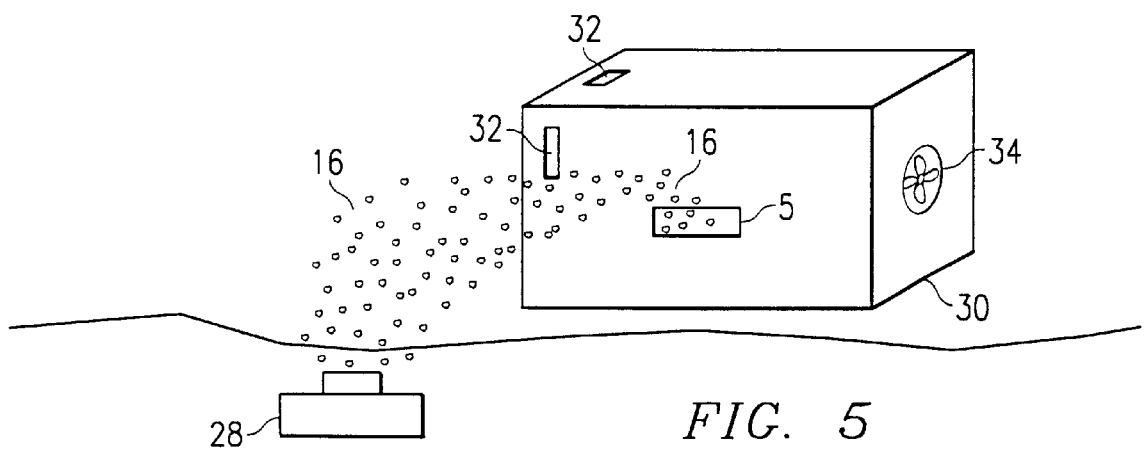
FIG. 5 is an illustrative embodiment of a vapor detector being used in a mine field.

Referring now to FIG. 5, the vapor detector 5 is shown in use in an area that contains one or more land mines 28. The vapor detector 5 is enclosed in a robust housing 30, which protects the vapor detector 5 from hostile environmental conditions such as rain, snow, sunlight and even wild animals. The housing 30 may be designed to shockproof the vapor detector 5 for deployment by airplane or parachute. The housing 30 may also use a self-righting design that ensures proper vapor detector 5 orientation if the vapor detector 5 is deployed by aircraft.

Land mine 28 contains an explosive that emits vapor 16, which emanates into vents 32 in the housing 30 and exposes vapor detector 5. Vapor 16 reacts with chemicals within waveguide 10. Light 14 transmitted through waveguide 10 is partially absorbed by the reactants and is detected by light detector 18. Light detector 18 signals the presence of land mine 28 in the area.

The housing 30 may also be fitted with a fan 34. The fan 34 operates to increase air flow from the surrounding area across the waveguide 10. The fan 34 decreases the time necessary for the vapor detector 5 to detect vapor 16 in an area. The fan 34 also increases the sensitivity and range of the vapor detector 5 by exposing the waveguide 10 to a larger volume of air and vapor 16 within the area.

The housing 30 also contains a power supply for the circuitry of the vapor detector 5 and the fan 34. The power supply may be a battery, solar power or a combination of battery and solar power.

Figure 6:
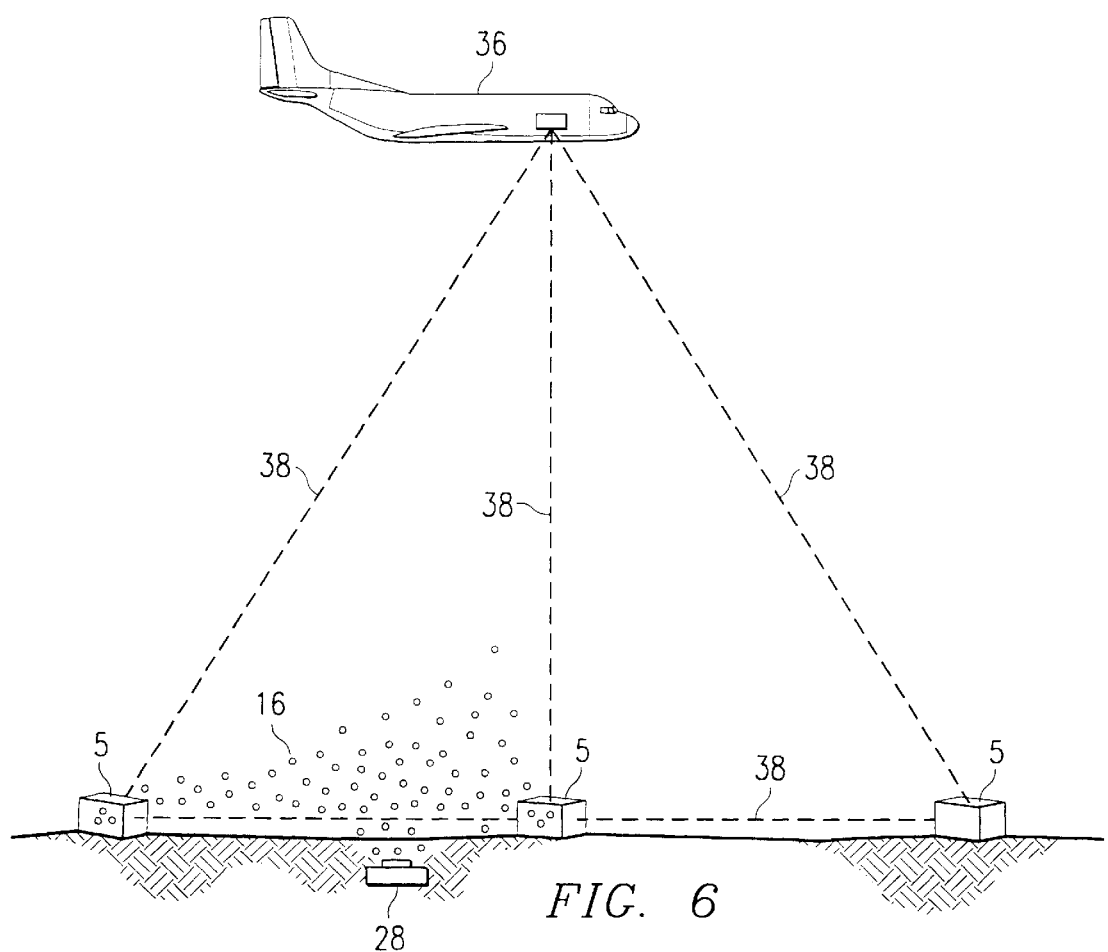
FIG. 6 is an illustrative embodiment of a network of vapor detectors being used in a mine field.

Referring now to FIG. 6, a system of networked vapor detectors 5 includes two or more vapor detectors 5. The vapor detectors 5 are capable of transmitting information from the light detector 18 of the vapor detector 5 to a receiver 36. Data from vapor detectors 5 is transmitted over a connection 38 to the receiver 36. Connection 38 may be a number of methods such as wire, fiber optics, visible light, radio frequency, infrared light, CDMA or NDMA.

Multiple vapor detectors 5 may be connected together in a net by wire connections 38. A vapor detector 5 may also communicate with other vapor detectors 5 to create redundancy in the network. Vapor detectors 5 may transmit their data to the receiver 36 via other vapor detectors 5. The receiver 36 may also be configured to control the function of vapor detectors 5 through the connections 38. The receiver 36 may signal the vapor detectors 5 to cease detecting during the daytime to avoid stray light corrupting the data. The receiver 36 could also signal the vapor detectors 5 to cease detecting to conserve power during periods of inactivity in an area.

This redundancy also allows network integrity in "line of sight" communication technologies. A first vapor detector 5 in a network may not "see" the receiver 36, and therefore not be capable of establishing connection 38 with the receiver. The first vapor detector 5 may, however, establish a connection 38 with a neighboring vapor detector 5 that has a connection 38 with the receiver 36. The neighboring vapor detector 5 may relay data from the first vapor detector 5 through the connection 38 to the receiver 36.

Receiver 36 may compile and analyze data from the vapor detectors 5 to determine the presence and location of landmine 28. Each vapor detector 5 in a network may be identified with a identification code. This identification code allows the receiver 36 to determine which data corresponds to a particular vapor detector 5.

The vapor detectors 5 may also be fitted with global positioning circuitry to ascertain the exact position of a particular vapor detector 5. The position of vapor detector 5 is transmitted to receiver 36, which may map the coordinates of all of the vapor detectors 5 within a network or an area. The position of land mine 28 may be determined by analyzing transmitted vapor 16 intensity information from all vapor detectors 5. The location of the land mine 28 corresponds to the locations of the vapor detectors 5 that transmit the highest concentrations of vapor 16.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A vapor detecting system, comprising:
   a light transparent waveguide infused with a material which reacts with a vapor to be detected to alter the light transparency of the waveguide;
   a light source for passing light through the waveguide; and
   a detector for detecting and evaluating changes in the light passing through the waveguide to determine the existence of the vapor to be detected.

2. The system of claim 1 wherein the waveguide is PVC, the infused material is Jeffamine T-403 and the vapor is a polynitroaromatic compound.

3. The system of claim 2 wherein the polynitroaromatic compound is TNT.

4. The system of claim 1 further including means disposed between said light source and said waveguide to focus said light onto said waveguide and a light block to block impingement of stray light onto said waveguide.

5. The system of claim 4 further including a reflective region disposed along a length of said waveguide to enhance the intensity of said light within said waveguide.

6. A vapor detecting system, comprising:
   a plurality of light transparent waveguides, each infused with a different material which reacts with a different vapor to be detected to alter the light transparency of the waveguides;
   means for passing light through the waveguides; and
   a separate detector for each waveguide for detecting and evaluating changes in the light passing through each waveguide to determine the existence of the vapors to be detected.

7. The system of claim 6 wherein said means for passing light through the waveguides comprises a separate light source for each of said waveguides, each said light source having a different light frequency.

8. The system of claim 7 wherein the material infused in each of said waveguides is reactive to the light frequency passing through the waveguide when the vapor to be detected is reacted with the infused material.

9. A radiation detecting system, comprising:
   a light transparent waveguide infused with a material which emits light when exposed to radiation to be detected; and
   a detector for detecting and evaluating changes in the light passing through the waveguide to determine the existence of the radiation to be detected.

10. The system of claim 9 wherein the infused material is a scintillation chemical.

11. The system of claim 1 further including a housing containing said light transparent waveguide infused with a material which reacts with a vapor to be detected to alter the light transparency of the waveguide, said light source for passing light through the waveguide and said detector for detecting and evaluating changes in the light passing through the waveguide to determine the existence of the vapor to be detected and a fan within said housing for increasing air flow across said waveguide.

12. A system for vapor detection which comprises:
    a plurality of spaced apart detector systems, each detector system comprising a housing, each housing containing a light transparent waveguide infused with a material which reacts with a vapor to be detected to alter the light transparency of the waveguide, a light source for passing light through the waveguide and a detector for detecting and evaluating changes in the light passing through the waveguide to determine the existence of the vapor to be detected;
    each housing containing means for transmitting information from the detector to a remote location.

13. The system of claim 12 further including a wire interconnecting said detector systems.

14. The system of claim 12 wherein each of said detector system includes means to transmit an address to indicate the detector system from which the transmitted information emanates.

15. A vapor detecting method, comprising the steps of:
    providing a light transparent waveguide infused with a material which reacts with a vapor to be detected to alter the light transparency of the waveguide;
    passing a light through the waveguide; and
    detecting and evaluating changes in the light passing through the waveguide to determine the existence of the vapor to be detected.

16. The method of claim 15, further including focussing said light onto said waveguide and blocking impingement of stray light onto said waveguide.

17. The method of claim 16 further including providing a reflective region disposed along a length of said waveguide to enhance the intensity of said light within said waveguide.

18. A vapor detecting method, comprising the steps of:
    providing a plurality of light transparent waveguides, each infused with a different material which reacts with a different vapor to be detected to alter the light transparency of the waveguides;
    passing light through the waveguides; and
    detecting and evaluating changes in the light passing through each waveguide to determine the existence of the vapors to be detected.

19. The method of claim 18 wherein said means for passing light through the waveguides comprises a separate light source for each of said waveguides, each said light source having a different light frequency.

20. The method of claim 19 wherein the material infused in each of said waveguides is reactive to the light frequency passing through the waveguide when the vapor to be detected is reacted with the infused material.

* * * * *